(12) United States Patent
Osumi et al.

(10) Patent No.: US 10,405,833 B2
(45) Date of Patent: Sep. 10, 2019

(54) ULTRASONIC DIAGNOSTIC APPARATUS AND PROBE PRESSURIZATION/DEPRESSURIZATION INFORMATION DISPLAY METHOD

(71) Applicant: Toshiba Medical Systems Corporation, Otawara-shi (JP)

(72) Inventors: Ryota Osumi, Nasushiobara (JP); Tetsuya Kawagishi, Kawasaki (JP); Yasuhiko Abe, Otawara (JP); Toshie Maruyama, Yaita (JP)

(73) Assignee: Canon Medical Systems Corporation, Otawara-shi (JP)

( * ) Notice: Subject to any disclaimer, the term of this patent is extended or adjusted under 35 U.S.C. 154(b) by 689 days.

(21) Appl. No.: 14/956,946

(22) Filed: Dec. 2, 2015

(65) Prior Publication Data

US 2016/0081664 A1 Mar. 24, 2016

Related U.S. Application Data

(63) Continuation of application No. PCT/JP2014/064850, filed on Jun. 4, 2014.

(30) Foreign Application Priority Data

Jun. 5, 2013 (JP) .................. 2013-118664

(51) Int. Cl.
*A61B 8/08* (2006.01)
*A61B 8/14* (2006.01)
*A61B 8/00* (2006.01)

(52) U.S. Cl.
CPC .............. *A61B 8/5223* (2013.01); *A61B 8/14* (2013.01); *A61B 8/463* (2013.01); *A61B 8/485* (2013.01);
(Continued)

(58) Field of Classification Search
CPC ........... A61B 8/14; A61B 8/463; A61B 8/485; A61B 8/488; A61B 8/5207; A61B 8/5223; A61B 8/08
See application file for complete search history.

(56) References Cited

U.S. PATENT DOCUMENTS

2006/0025688 A1* 2/2006 Hayase .................... A61B 8/06
600/454
2010/0041994 A1 2/2010 Abe
(Continued)

FOREIGN PATENT DOCUMENTS

| JP | 2009-195613 | 9/2009 |
|---|---|---|
| JP | 2011-25011 | 2/2011 |
| JP | 2011-120614 | 6/2011 |

OTHER PUBLICATIONS

International Search Report dated Jul. 8, 2014 in PCT/JP2014/064850, filed on Jun. 4, 2014 (with English Translation).
(Continued)

*Primary Examiner* — Bo Joseph Peng
(74) *Attorney, Agent, or Firm* — Oblon, McClelland, Maier & Neustadt, L.L.P.

(57) ABSTRACT

An ultrasonic diagnostic apparatus according to an embodiment generates, based on the echo signal, velocity distribution information of a tissue in the object. The ultrasonic diagnostic apparatus generates state information representing a cycle of the pressurization or the depressurization and target information representing a target cycle of pressurization or depressurization based on the velocity distribution information. The ultrasonic diagnostic apparatus associates one of two variables defining a predetermined graphic pattern with the cycle, displays the state information and the target information as the graphic pattern, and displays the graphic pattern upon deforming a shape of the graphic pattern in accordance with a change in the cycle of the
(Continued)

pressurization or the depressurization in the state information.

11 Claims, 9 Drawing Sheets

(52) U.S. Cl.
CPC ............ *A61B 8/488* (2013.01); *A61B 8/5207* (2013.01); *A61B 8/08* (2013.01)

(56) References Cited

U.S. PATENT DOCUMENTS

2010/0331691 A1   12/2010   Okamura et al.
2012/0016238 A1   1/2012    Matsumura

OTHER PUBLICATIONS

Written Opinion dated Jul. 8, 2014 in PCT/JP2014/064850, filed on Jun. 4, 2014.

* cited by examiner

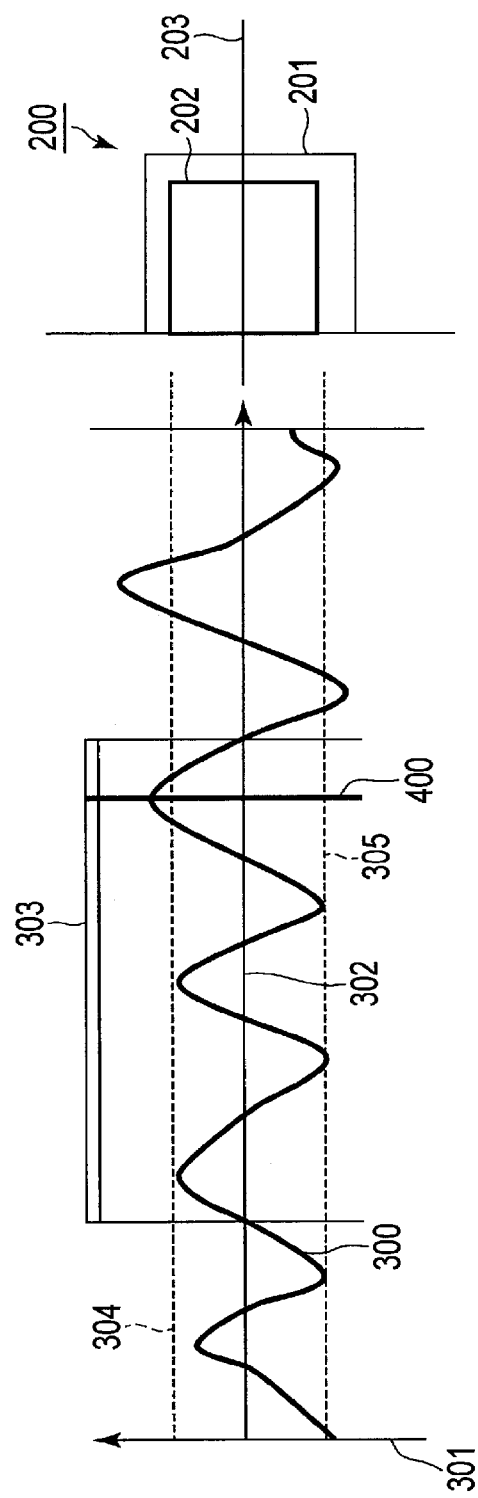
F I G. 6

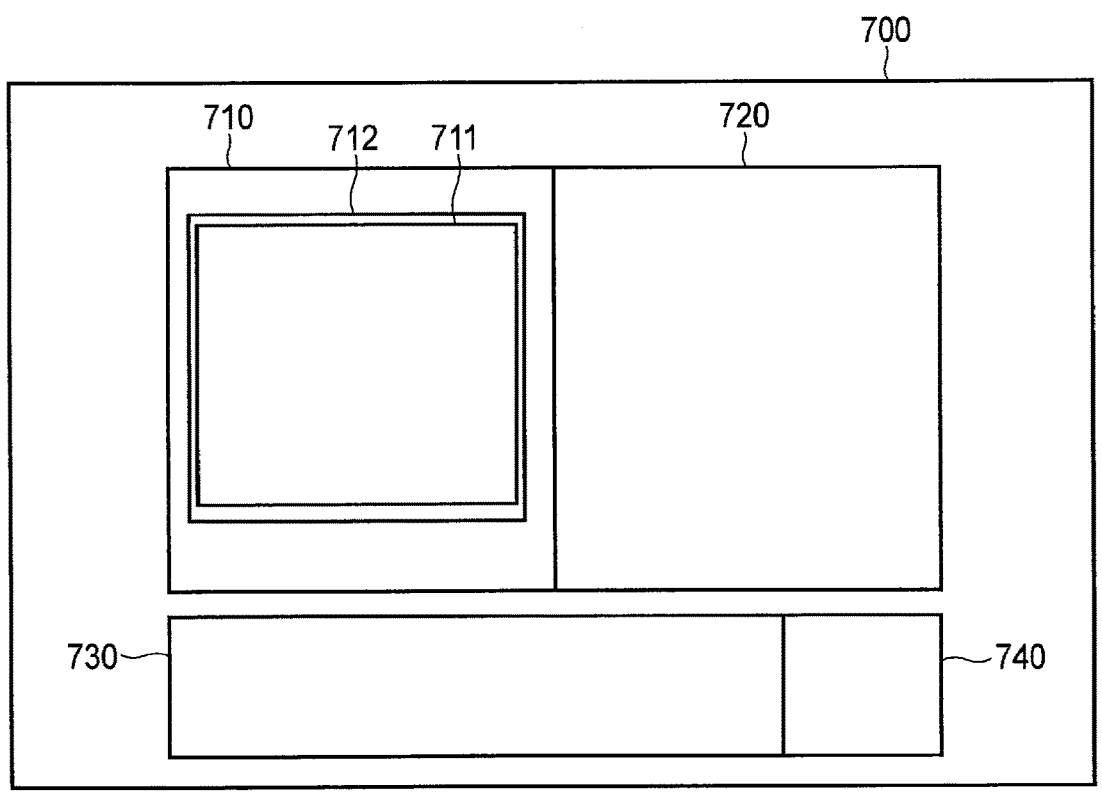
F I G. 9

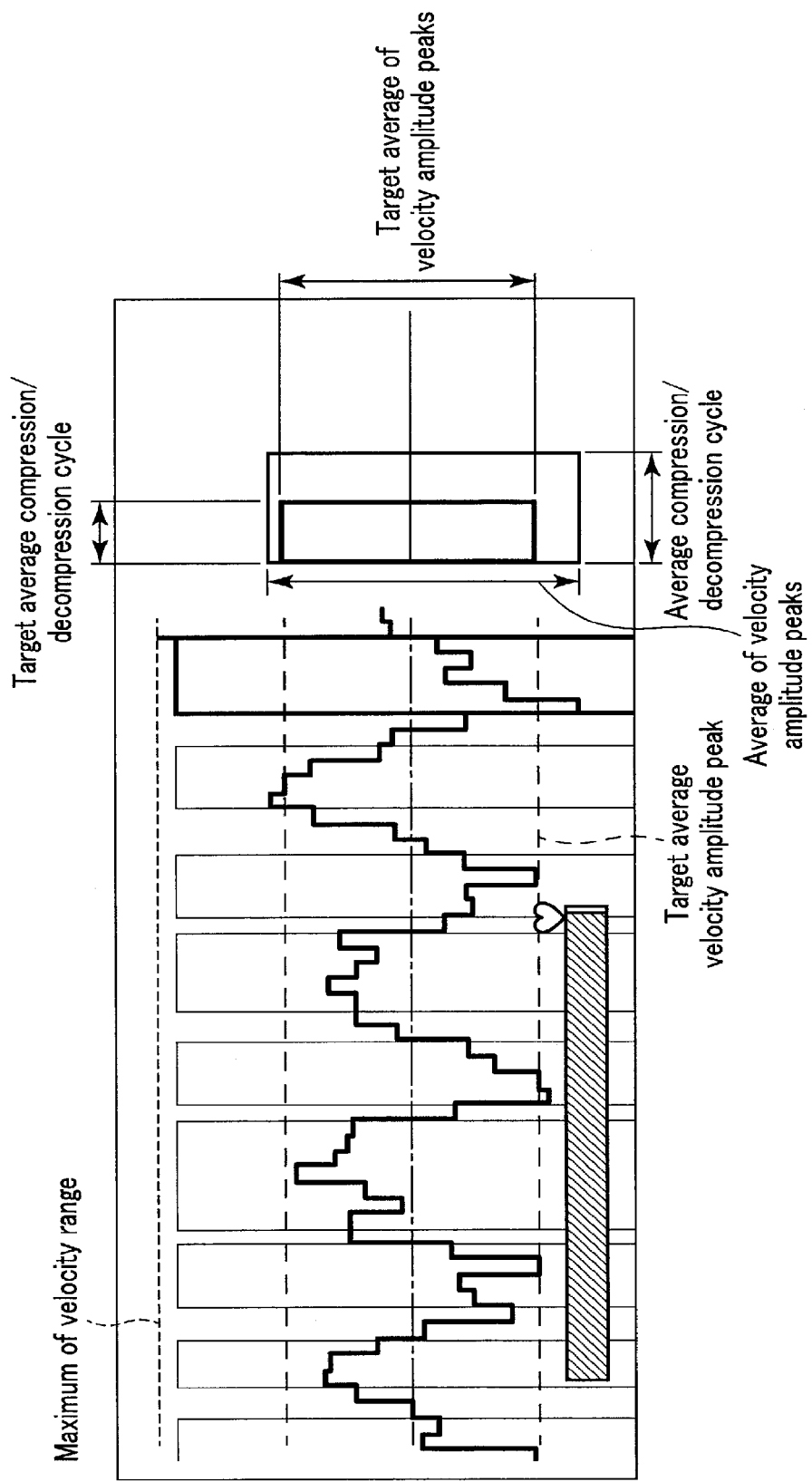
F I G. 11

ULTRASONIC DIAGNOSTIC APPARATUS AND PROBE PRESSURIZATION/DEPRESSURIZATION INFORMATION DISPLAY METHOD

CROSS-REFERENCE TO RELATED APPLICATIONS

This application is a Continuation application of PCT application No. PCT/JP2014/064850, filed on Jun. 4, 2014, and is based upon and claims the benefit of priority from Japanese Patent Application No. 2013-118664, filed on Jun. 5, 2013, the entire contents of which are incorporated herein by reference.

FIELD

Embodiments described herein relate generally to an ultrasonic diagnostic apparatus and a probe pressurization/depressurization information display method.

BACKGROUND

In ultrasonic diagnosis, how the heart beats or the fetus moves is displayed in real time by simply bringing an ultrasonic probe into contact with the body surface. Ultrasonic diagnosis is highly safe, and hence allows repetitive examination. In addition, a system in ultrasonic diagnosis is smaller in size than other diagnostic apparatuses such as an X-ray diagnostic apparatus, CT apparatus, and MRI apparatus, and hence can be moved to the bedside to be easily and conveniently used for examination. For this reason, ultrasonic diagnosis can be said to be a simple diagnostic technique.

Ultrasonic diagnostic apparatuses for performing such ultrasonic diagnosis vary in type depending on the types of functions incorporated in the ultrasonic diagnostic apparatuses. Of these ultrasonic diagnostic apparatuses, some compact apparatuses which have already been developed are small enough to be carried with one hand. Ultrasonic diagnosis is free from the influence of radiation exposure unlike diagnosis using X-rays. Therefore, such ultrasonic diagnostic apparatuses can be used in obstetrics, medical care at home, and the like.

An ultrasonic diagnostic apparatus emits, into an object, ultrasonic pulses generated from the ultrasonic transducers incorporated in an ultrasonic probe. The ultrasonic diagnostic apparatus receives reflected waves from the object tissue via the ultrasonic transducers, and generates and displays image data and the like. Using such an ultrasonic diagnostic apparatus allows an operator such as a doctor to perform image diagnosis for an object.

As an image diagnostic technique using an ultrasonic diagnostic apparatus, there is available a technique in which the operator compresses/decompresses (pressurizing/depressurizing operation) an object tissue by using the ultrasonic probe and the generated strain information (to be written as strain distribution information hereinafter) concerning the object tissue is calculated as hardness information concerning the tissue.

In order to calculate strain distribution information, such an ultrasonic diagnostic apparatus needs to detect the displacement or moving velocity of the tissue in accordance with the compression/decompression of the tissue. The displacement or moving velocity of the tissue is detected by, for example, a method of detecting the displacement of the tissue between adjacent frames based on the cross-correlation between signals (reception RF signals) received via the ultrasonic probe, a method of detecting the moving velocity of the tissue by the Doppler method, or a method combining such methods.

In this case, to properly obtain the above strain distribution information, the operator needs to compress/decompress the tissue by using the ultrasonic probe with proper strength in a proper cycle. That is, since the accuracy of strain distribution information depends on operation by the operator, it is preferable to feed back the state of compression/decompression by the operator to him/her in order to obtain proper strain distribution information.

In contrast to this, there is known a technique of presenting a waveform representing the state (strength and cycle) of compression/decompression by the operator. This allows the operator to check the state of compression/decompression by his/her operation.

However, presenting only a waveform representing the state of compression/decompression by the operator may not allow the operator to grasp the proper degree of compression/decompression. This may lead to a failure to obtain proper strain distribution information.

It is an object to provide an ultrasonic diagnostic apparatus which enables the operator to perform proper compression/decompression and a probe pressurization/depressurization information display method which can display proper compression/decompression to the operator.

BRIEF DESCRIPTION OF THE DRAWINGS

FIG. 6 is a view showing an example of the display form of index information displayed together with an average moving velocity waveform in the cine mode according to the first embodiment.

FIG. 9 is a view showing an example of the layout of a display screen when displaying an index determination result according to the second embodiment.

FIG. 11 is an enlarged view of a portion in FIG. 10 according to the first embodiment.

DETAILED DESCRIPTION

In general, according to one embodiment, an ultrasonic diagnostic apparatus includes an ultrasonic probe, a transmission/reception circuitry, a velocity distribution information generation circuitry, an index information generation circuitry, and a display.

The transmission/reception circuitry transmits an ultrasonic wave to an object and receives a reflected wave from the object as an echo signal via the ultrasonic probe.

The velocity distribution information generation circuitry generates, based on the echo signal, velocity distribution information of a tissue in the object which is associated with pressurization or depressurization with the ultrasonic probe.

The index information generation circuitry generates state information representing a cycle of the pressurization or the depressurization and target information representing a target cycle of pressurization or depressurization based on the velocity distribution information.

The display associates one of two variables defining a predetermined graphic pattern with the cycle, displays the state information and the target information as the graphic pattern, and displays the graphic pattern upon deforming a shape of the graphic pattern in accordance with a change in the cycle of the pressurization or the depressurization in the state information.

Each embodiment will be described below with reference to the accompanying drawings.

First Embodiment

An ultrasonic diagnostic apparatus according to the first embodiment will be described first. The ultrasonic diagnostic apparatus according to this embodiment is configured such that the operator performs compression (pressurization)/decompression (depressurization) on a tissue in an object by using the ultrasonic probe, and the information of the resultant strain in the tissue in the object is used as the hardness information of the tissue.

Figure 1:
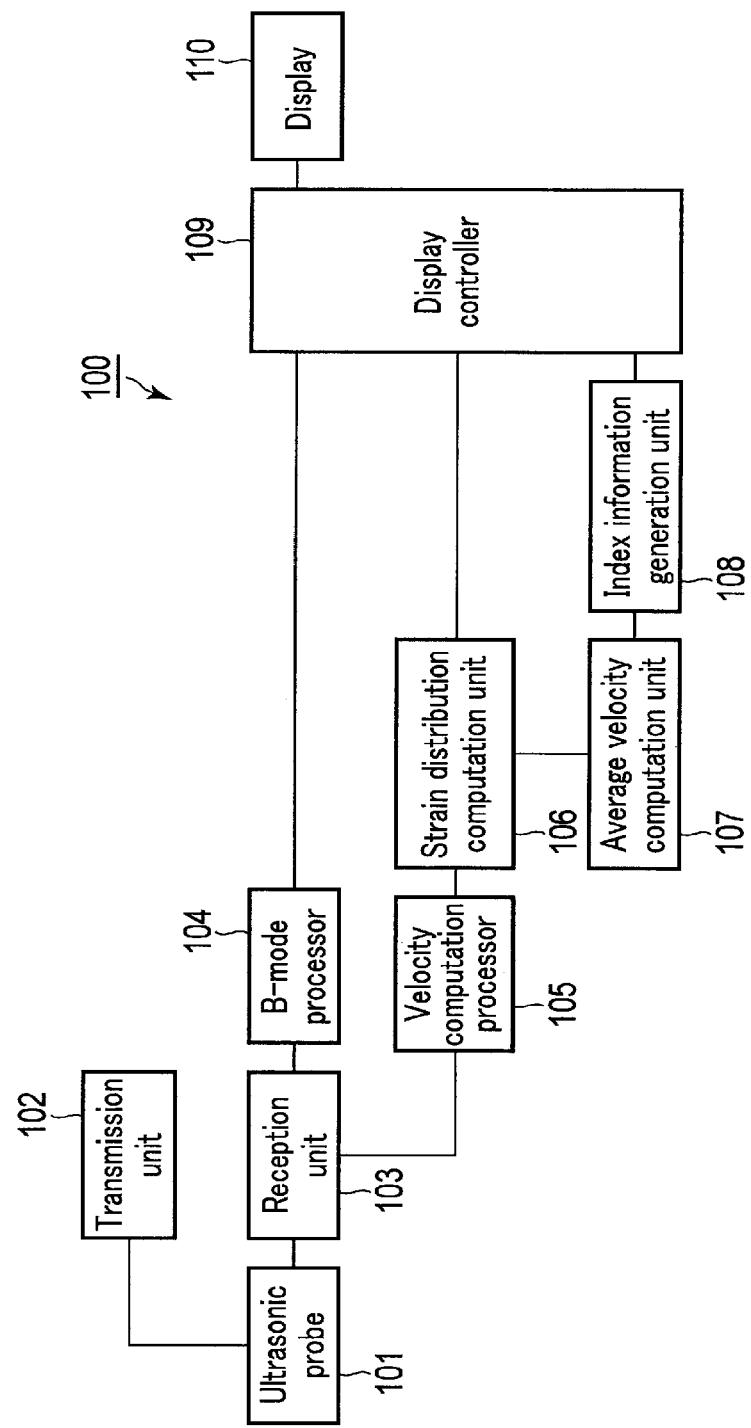
FIG. 1 is a block diagram showing the arrangement of an ultrasonic diagnostic apparatus 100 according to the first embodiment.

FIG. 1 is a block diagram showing the arrangement of an ultrasonic diagnostic apparatus 100 according to this embodiment. As shown in FIG. 1, the ultrasonic diagnostic apparatus 100 includes an ultrasonic probe 101, a transmission unit 102, a reception unit 103, a B-mode processor 104, a velocity computation processor 105, a strain distribution computation unit 106, an average velocity computation unit 107, an index information generation unit 108, a display controller 109, and a display 110.

Note that the ultrasonic diagnostic apparatus 100 according to this embodiment can be implemented by hardware such as integrated circuits or by software programs in the form of software modules. The function of each constituent element will be described below.

The ultrasonic probe 101 is a device (probe) which transmits and receives ultrasonic waves to irradiate an object and be reflected by it. The ultrasonic probe 101 includes a plurality of piezoelectric transducers (electromechanical reversible conversion elements), a matching layer, and a backing member. The plurality of piezoelectric transducers generate ultrasonic waves based on driving signals from the transmission unit 102, and convert reflected waves from the object into electrical signals. The matching layer is provided on the piezoelectric transducers. The backing member prevents ultrasonic waves from propagating backward from the piezoelectric transducers. With this arrangement, the ultrasonic probe 101 converts supplied driving signals (pulse driving voltages) into ultrasonic pulse signals, transmits them in a desired direction in a scan area in an object, and converts reflected waves (ultrasonic waves) from the object into echo signals of corresponding voltages.

The transmission unit 102 transmits a driving signal to each piezoelectric transducer of the ultrasonic probe 101 at a timing with a predetermined transmission delay time being added for each transmission channel. With this operation, the transmission unit 102 transmits an ultrasonic wave from each piezoelectric transducer of the ultrasonic probe 101 into an object. More specifically, the transmission unit 102 includes pulser circuitry and delay circuitry (neither of which is shown). The pulser circuitry repeatedly generates rate pulses for the formation of transmission ultrasonic waves at a predetermined rate frequency fr Hz (period: 1/fr sec). The delay circuitry gives each rate pulse a delay time necessary to focus an ultrasonic wave into a beam and determine transmission directivity for each channel. The transmission unit 102 applies a driving pulse to each transducer to form an ultrasonic beam toward a predetermined scanning line at the timing based on this rate pulse.

The reception unit 103 receives, via the ultrasonic probe 101 (each piezoelectric transducer), an ultrasonic echo containing, for example, components reflected by a discontinuity surface of acoustic impedance in the object and scattered by scatterers in the tissue in accordance with the transmission of ultrasonic waves. The reception unit 103 performs reception delay and addition processing for echo signals corresponding to received ultrasonic echoes. The reception unit 103 outputs the echo signal obtained by the addition processing to the B-mode processor 104 and the velocity computation processor 105.

More specifically, the reception unit 103 includes amplification circuitry, an A/D (Analog/Digital) converter, and an adder (none of which are shown). The amplification circuitry amplifies an echo signal received via the ultrasonic probe 101 for each channel. The A/D converter gives a delay time necessary to decide reception directivity to each amplified echo signal. The adder performs addition processing for echo signals to which delay times are given. This addition generates an echo signal corresponding to a predetermined scanning line.

The B-mode processor 104 generates, as the morphological information of a tissue in an object, a B-mode signal corresponding to the amplitude intensity of an ultrasonic echo by performing envelope detection processing for an echo signal output from the reception unit 103.

The velocity computation processor (velocity distribution information generation circuitry) 105 generates velocity distribution information concerning a tissue in an object, for which compression/decompression is performed by the operator using the ultrasonic probe 101, based on an echo signal output from the reception unit 103. The velocity computation processor 105 generates velocity distribution information concerning the tissue in the object in association with pressurization or depressurization with the ultrasonic probe 101 based on the echo signal.

More specifically, the velocity computation processor 105 performs quadrature detection processing, autocorrelation processing, and delay addition processing for the echo signal output from the reception unit 103, and generates, based on the Doppler shift components of the echo signal having undergone delay addition processing, tissue Doppler information representing a two-dimensional distribution in the tissue, which corresponds to the velocity, variance, and power of the tissue which is moving in the object. The velocity computation processor 105 extracts velocity components from the generated tissue Doppler information, and outputs the velocity components as velocity distribution information to the strain distribution computation unit 106.

The strain distribution computation unit 106 generates strain distribution information representing the strain of the tissue of the object which is caused by compression/decompression by the operator based on the velocity distribution information output from the velocity computation processor 105.

The average velocity computation unit (waveform generation circuitry) 107 computes the average moving velocity of the tissue, as the strength of compression/decompression by the operator, which corresponds to the strain distribution information generated by the strain distribution computation unit 106. Note that the average moving velocity of this tissue is computed based on the velocity distribution information output from the velocity computation processor 105.

The index information generation unit 108 generates, as index information for the operator, compression/decompression state information (state information) representing the state of compression (pressurization)/decompression (depressurization) by the operator and compression/decompression target information (target information) representing the target of compression (pressurization)/decompression (depressurization) based on the velocity distribution information (the average moving velocity of the tissue) output from the velocity computation processor 105.

That is, the index information generation unit 108 generates, as index information, state information representing the cycle of pressurization or depressurization and target information representing the target cycle of pressurization or depressurization based on the velocity distribution information. Note that state information may further include information representing the degree of pressurization or depressurization with the ultrasonic probe 101. In addition, target information may further include information representing the target degree of pressurization or depressurization.

Note that the index information generation unit 108 may generate cycle instruction information for bringing a cycle in state information close to that in target information based on the difference value between the cycle in the state information and that in the target information. If a cycle in state information is longer than that in target information, cycle instruction information includes, for example, information indicating "quickly". In contrast, if a cycle in state information is shorter than that in target information, cycle instruction information includes, for example, information indicating "slowly". If a cycle in state information is almost equal to that in target information, cycle instruction information includes, for example, information indicating "maintain cycle".

In addition, the index information generation unit 108 may generate degree instruction information for bringing the degree of pressurization (or depressurization) in state information close to that in target information based on the difference value between the degree of pressurization (or depressurization) in the state information and that in the target information. If the degree of pressurization (or, depressurization) in state information is larger than that in target information, degree instruction information includes, for example, information indicating "weakly". In contrast, if the degree of pressurization (or depressurization) in state information is smaller than that in target information, degree instruction information includes, for example, information indicating "strongly". If the degree of pressurization (or depressurization) in state information is almost equal to that in target information, degree instruction information includes, for example, information indicating "maintain pressurization (depressurization)".

The index information generation unit 108 outputs the generated cycle instruction information and degree instruction information to the display 110.

The display controller (image generation circuitry) 109 converts (scan-converts) a scanning line signal (ultrasonic B-mode/strain scanning line signal) obtained by ultrasonic scanning into a scanning line signal suitable for display (e.g., a scanning line signal in a general video format typified by a TV format or the like). That is, the display controller 109 generates ultrasonic diagnostic images (a B-mode image, a strain image, and the like) as display images based on the B-mode signal generated by the B-mode processor 104 and the strain distribution information generated by the strain distribution computation unit 106.

The display 110 presents (displays) the operator the ultrasonic diagnostic images (the B-mode image and the strain image) generated by the display controller 109 and the index information (the compression/decompression state information and the compression/decompression target information) generated by the index information generation unit 108.

Figure 2:
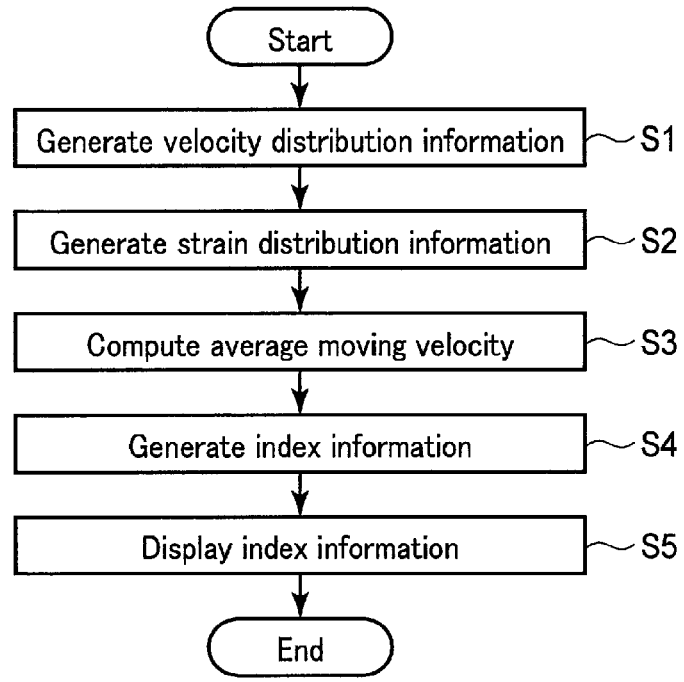
FIG. 2 is a flowchart showing a processing procedure when the ultrasonic diagnostic apparatus 100 according to the first embodiment generates index information.

A processing procedure to be followed when the ultrasonic diagnostic apparatus 100 according to this embodiment generates the above index information will be described next with reference to the flowchart of FIG. 2. The processing performed by the velocity computation processor 105, the strain distribution computation unit 106, the average velocity computation unit 107, the index information generation unit 108, and the display 110 included in the ultrasonic diagnostic apparatus 100 will be mainly described here. Note that in the following description, for the sake of convenience, the processing shown in FIG. 2 to be performed when generating index information will be referred to as index information generation processing.

Assume that in this embodiment, the operator continuously performs compression/decompression on an object tissue by using the ultrasonic probe 101 to use the strain information of the object tissue as the hardness information of the tissue.

In this case, the velocity computation processor 105 generates tissue Doppler information based on an echo signal output from the reception unit 103. In this case, the velocity computation processor 105 generates tissue Doppler information by executing quadrature detection processing, autocorrelation processing, and delay addition processing for the echo signal output from the reception unit 103. Note that the tissue Doppler information generated in this case is information corresponding to the velocity, variance, and power of the tissue which is moving in the object in accordance with compression/decompression (operation) by the operator, and is information representing a two-dimensional distribution in the tissue. The velocity computation processor 105 generates velocity distribution information concerning the object tissue (its velocity components) in accordance with compression/decompression by the operator using the generated tissue Doppler information (step S1).

The strain distribution computation unit 106 then calculates a displacement by performing temporal integration of the velocity distribution information generated by the velocity computation processor 105. The strain distribution computation unit 106 computes the local strain of the tissue by performing a predetermined computation using the calculated displacement. The strain distribution computation unit 106 converts the local strain values of the tissue obtained as a result of the computation into color codes, and maps them at corresponding positions. The strain distribution computation unit 106 generates strain distribution information by converting the strain values into color codes and mapping them (step S2). Note that the strain distribution information generated by the strain distribution computation unit 106 represents the strain (its distribution) of the object tissue caused by compression/decompression by the operator.

The average velocity computation unit 107 computes the average moving velocity of the tissue in a region corresponding to the strain distribution information generated by the strain distribution computation unit 106, based on the velocity distribution information generated by the velocity computation processor 105 (step S3).

The index information generation unit 108 generates information (index information) as an index for compression (pressurization)/decompression (depressurization) by the operator based on the calculation result (the average moving velocity of the tissue) computed by the average velocity computation unit 107 (step S4). The index information generated by the index information generation unit 108 includes compression/decompression state information representing the state of compression/decompression by the operator and compression/decompression target information representing the target of the compression/decompression.

Compression/decompression state information is information representing the strength (magnitude/degree) and cycle of compression/decompression by the operator as the state of compression/decompression by the operator. On the other hand, compression/decompression target information is information representing the target strength (magnitude/degree) and cycle of compression/decompression. The strength of compression/decompression by the operator is represented by the average moving velocity of the tissue in the object for which compression/decompression has been performed by the operator. Likewise, the target strength of compression/decompression is represented by the target average moving velocity of the tissue in the object in compression/decompression. Assume that the target strength and cycle of compression/decompression is the strength and cycle of compression/decompression which can obtain proper strain distribution information, and is determined in advance (set in advance) in the ultrasonic diagnostic apparatus 100.

The display 110 then displays the index information (compression/decompression state information and compression/decompression target information) generated by the index information generation unit 108 on a display device in a predetermined form at a predetermined timing. With this operation, the index information is presented to the operator (step S6). In this case, the display 110 displays the compression/decompression state information and the compression/decompression target information as graphic patterns which can be compared with each other. Note that the display device is, for example, a CRT display, liquid crystal display, organic EL display, or plasma display.

In addition, the display 110 displays the index information together with an ultrasonic diagnostic image. In this embodiment, the ultrasonic diagnostic image displayed together with the index information includes, for example, a B-mode image and a strain image. The display controller 109 generates a B-mode image based on a B-mode signal generated by the B-mode processor 104. Note that a B-mode image is an image representing the intensity of reflected waves from an object by luminance. On the other hand, the display controller 109 generates a strain image based on strain distribution information generated by the strain distribution computation unit 106 as described above. Processing associated with the B-mode image and strain image is executed in parallel with the above index information generation processing.

The display 110 superimposes and displays this strain image on the B-mode image. The display 110 also displays a marker for indicating an anatomical position on the image or a color bar indicating the magnitudes of strain converted into color codes. In addition, the display 110 displays index information.

The display form of the above index information (the compression/decompression state information and the compression/decompression target information) will be described in detail below. Assume that in the following description, the above average moving velocity of the object tissue is used as the strength of compression/decompression.

Figure 3:
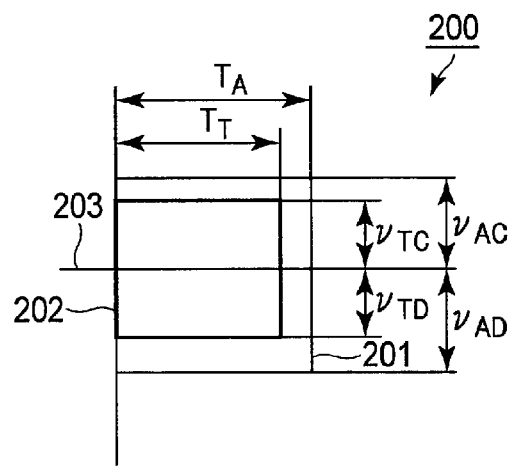
FIG. 3 is a view showing an example of the display form of index information displayed in graphics according to the first embodiment.

First of all, FIG. 3 shows an example of the display form of index information displayed in graphics according to this embodiment. In the example shown in FIG. 3, index information (a predetermined graphic pattern representing index information) 200 is constituted by graphic patterns 201 and 202 each having a rectangular shape.

Note that each predetermined graphic pattern is not limited to a rectangular shape and may be, for example, elliptic. In more general, each predetermined graphic pattern is an arbitrary graphic pattern (e.g., a triangle, rhombus, or parallelogram) defined by two variables (parameters). One of two variables is associated with the cycle of pressurization or depressurization in target information and state information. The other of the two variables is associated with the degree of pressurization or depressurization in the target information and the state information. In addition, index information may be displayed as a predetermined function whose shape is defined by two variables. The predetermined function is, for example, a Gaussian function or logistic function.

The display 110 deforms and displays the shape of a predetermined graphic pattern or predetermined function concerning state information in accordance with the degree of pressurization/depressurization in the state information. Note that the display 110 changes the unit length scales of two sides perpendicular to each other (the first and second sides (to be described later)) of a rectangle indicating index information in accordance with the type of the ultrasonic probe 101 or a diagnosis target region of an object, and displays the resultant rectangle.

Note that the display 110 may display character strings concerning cycle instruction information and degree instruction information as a sentence in a display area different from the graphic display area indicating an ultrasonic diagnostic image and index information concerning an echo signal. Character strings are those which indicate cycle instruction information and degree instruction information in parallel. Character strings have, for example, nine patterns: "slowly/weakly", "slowly/strongly", "quickly/weakly", "quickly/strongly", "maintain cycle/weakly", "maintain cycle/strongly", "slowly/maintain pressurization (depressurization)", "quickly/maintain pressurization (depressurization)", and "maintain cycle/maintain pressurization (depressurization)". Note that the display 110 may display cycle instruction information and degree instruction information via the ultrasonic probe 101 as navigation information for the timing and degree of pressurization/depressurization with respect to an object.

The display 110 further includes an output unit which outputs audible sounds corresponding to state information and target information. More specifically, the output unit outputs an audible sound having a sound volume and a frequency which correspond to the degree of pressurization (or depressurization) in the state information at time intervals corresponding to the cycle in the state information. In addition, the output unit outputs an audible sound having a sound volume and a frequency which correspond to the degree of pressurization (or depressurization) in the target information at time intervals corresponding to the cycle in the target information. Note that the output unit may output character strings concerning cycle instruction information and degree instruction information in the form of audible sounds. Note that the output unit can also output the above navigation information in the form of audible sounds.

The graphic pattern 201 in FIG. 3 represents compression/decompression state information included in index information. That is, the graphic pattern 201 represents the average moving velocity of the tissue corresponding to the compression (pressurization)/decompression (depressurization) by the operator and the cycle of compression/decompression by the operator. More specifically, referring to the graphic pattern 201, a portion, of the longitudinal length (first side) of the graphic pattern 201, which is located above a reference axis 203 represents a velocity $v_{AC}$ at the time of compression, and a portion, of the longitudinal length, which is located below the reference axis 203 represents a velocity $v_{AD}$ at the time of decompression. The velocity $v_{AC}$ at the time of compression corresponds to the degree of pressurization by the operator. The velocity $v_{AD}$ at the time of decompression corresponds to the degree of depressurization by the operator. In addition, referring to the graphic pattern 201, the transverse length (the second side adjacent to the first side) of the graphic pattern 201 represents a cycle $T_A$ of compression/decompression by the operator.

On the other hand, the graphic pattern 202 in FIG. 3 represents compression/decompression target information included in index information. That is, the graphic pattern 202 represents the target average moving velocity of the tissue corresponding to compression (pressurization)/decompression (depressurization) and the target cycle of compression/decompression. More specifically, referring to the graphic pattern 202, a portion, of the longitudinal length of the graphic pattern 202, which is located above the reference axis 203 represents a target velocity $v_{TC}$ at the time of compression, and a portion, of the longitudinal length, which is located below the reference axis 203 represents a target velocity $v_{TD}$ at the time of decompression. The target velocity $v_{TC}$ at the time of compression corresponds to the target degree of pressurization. The velocity $v_{TD}$ at the time of decompression corresponds to the target degree of depressurization.

Figure 4:
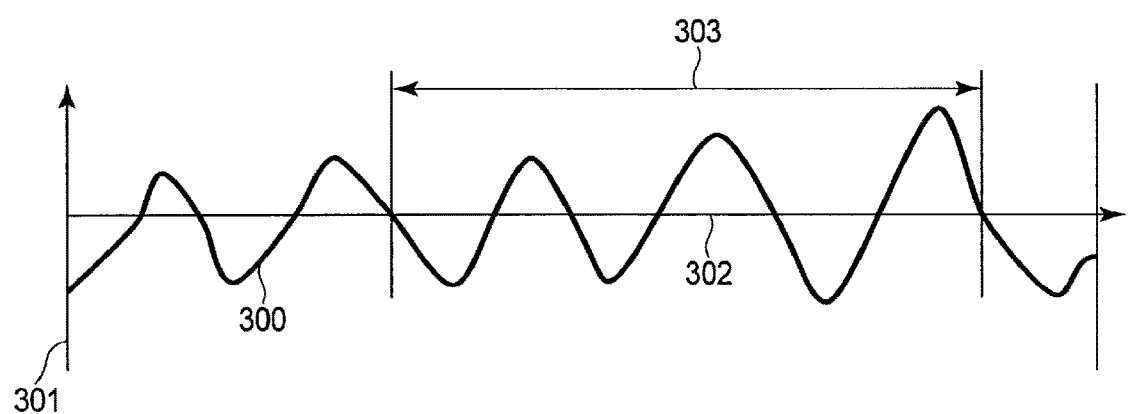
FIG. 4 is a graph showing a waveform representing a temporal change in the average moving velocity of a tissue which corresponds to compression/decompression by the operator according to the first embodiment.

FIG. 4 shows a waveform (to be written as an average moving velocity waveform hereinafter) 300 representing a temporal change in the average moving velocity of the tissue in accordance with compression/decompression by the operator. This average moving velocity waveform can be generated based on the average moving velocity of the tissue computed by the average velocity computation unit 107. Referring to the average moving velocity waveform shown in FIG. 4, a temporal change in the average moving velocity of the tissue is depicted with an ordinate 301 representing the average moving velocity of the tissue, and an abscissa 302 representing the time.

The above velocity $v_{AC}$ at the time of compression and the above velocity $v_{AD}$ at the time of decompression are calculated from average values, effective values, or peak values at the time of compression and at the time of decompression in the most recent interval having a predetermined wave number (e.g., an interval 303 in FIG. 4) based on the average moving velocity waveform shown in FIG. 4. Assume that the cycle $T_A$ of compression/decompression by the operator is a one-wave cycle or the average cycle of a predetermined wave number on the average moving velocity waveform 300. Assume that the starting point and finishing point of the measurement of a cycle each are, for example, a point where the average moving velocity of the tissue on the average moving velocity waveform 300 becomes 0 (zero) or a peak value.

As described above, the most recent average moving velocity is used to calculate the velocity $v_{AC}$ at the time of compression, the velocity $v_{AD}$ at the time of decompression, and the cycle $T_A$ of compression/decompression by the operator. For this reason, the graphic pattern 201 (i.e., the compression/decompression state information) of the index information (the compression/decompression state information and the compression/decompression target information) 200 is updated (i.e., newly generated) in accordance with the lapse of an ultrasonic diagnosis time.

Displaying (presenting) the index information 200 shown in FIG. 3 allows the operator to perform ultrasonic diagnosis while comparing the graphic pattern 201 representing the compression/decompression state information with the graphic pattern 202 representing the compression/decompression target information. This enables the operator to operate the ultrasonic probe 101 so as to match the graphic pattern 201 (compression/decompression state information) with the graphic pattern 202 (compression/decompression target information). With this operation, the ultrasonic diagnostic apparatus 100 can easily obtain proper strain distribution information.

Figure 5:
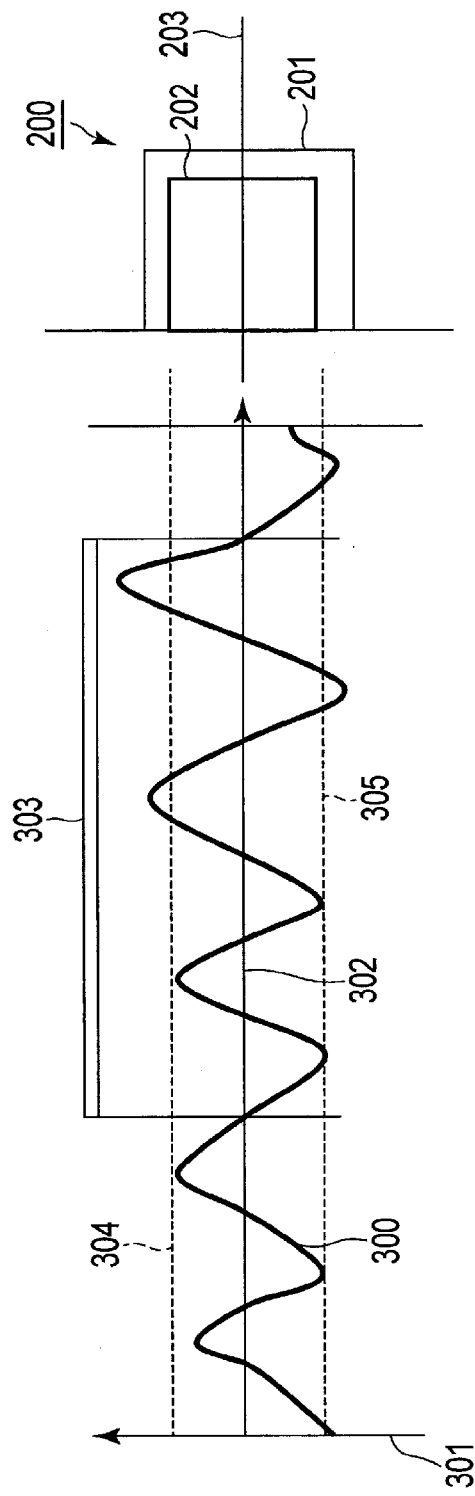
FIG. 5 is a view showing an example of the display form of index information displayed together with an average moving velocity waveform according to the first embodiment.

Note that the ultrasonic diagnostic apparatus 100 may be configured to display the above average moving velocity waveform 300 shown in FIG. 4 together with the index information 200. FIG. 5 is a graph showing an example of the display form of index information displayed together with an average moving velocity waveform.

In the example shown in FIG. 5, the display 110 displays the index information 200 (the graphic patterns 201 and 202) on the right side of the average moving velocity waveform 300. In this case, as shown in FIG. 5, visibility for the operator is improved by arranging the reference axis 203 of the index information 200 (the graphic patterns 201 and 202) and the abscissa 302 of the average moving velocity waveform 300 on the same line. In addition, displaying a broken line 304 representing the target velocity $v_{TC}$ at the time of compression, a broken line 305 representing the target velocity $v_{TD}$ at the time of decompression, and the like on the average moving velocity waveform 300 allows the operator to easily grasp the relationship between the index information 200 and the average moving velocity waveform 300. Note that, as shown in FIG. 5, the interval 303 necessary for the calculation of the above compression/decompression state information (the velocity at the time of compression, the velocity at the time of decompression, and the cycle of compression/decompression by the operator) may be displayed to allow the operator to visually recognize it.

In this case, when operating in the cine mode (the mode of repeatedly displaying a plurality of images belonging to a predetermined period including the generation time points of images), the ultrasonic diagnostic apparatus 100 can display, for example, an image, of ultrasonic diagnostic images obtained in ultrasonic diagnosis, which corresponds to a predetermined phase designated by the operator. At this time, the index information generation unit 108 generates state information based on velocity distribution information in a period during which the cine mode is executed.

FIG. 6 is a view showing an example of the display form of index information displayed together with an average moving velocity waveform in the cine mode. It is possible to specify a phase by moving a phase cursor 400 shown in FIG. 6 on the average moving velocity waveform 300 in the cine mode. Assume that in this case, when calculating the velocity $v_{AC}$ at the time of compression, the velocity $v_{AD}$ at the time of decompression, and the cycle $T_A$ of compression/decompression by the operator, the interval 303 (the average moving velocity and the cycle in it) including the phase cursor 400 (a phase specified by it) as shown in FIG. 6 is used. This allows the operator to grasp the state of compression/decompression concerning a displayed image.

Figure 7:
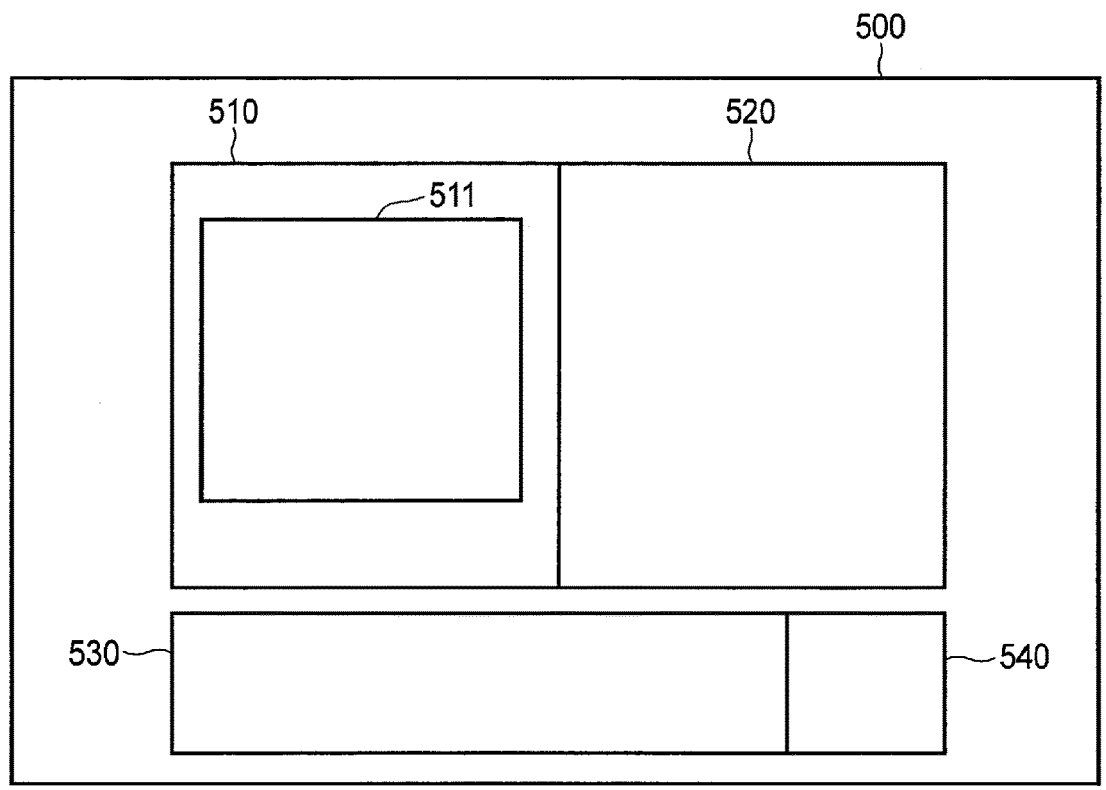
FIG. 7 is a view showing an example of the layout of a display screen when displaying index information together with an average moving velocity waveform according to the first embodiment.

FIG. 7 shows an example of the layout of a display screen when displaying the above index information together with an average moving velocity waveform. As shown in FIG. 7, areas 510 to 540 are arranged on a display screen 500.

For example, a B-mode image is displayed in the area 510. A strain image is displayed in the area 511 provided in the area 510. That is, the strain image is displayed in the area 511 while being superimposed on the B-mode image. On the other hand, a B-mode image is displayed for reference in the area 520.

The average moving velocity waveform described with reference to FIG. 4 is displayed in the area 530. The index information described with reference to FIG. 2 is displayed in the area 540. In the areas 530 and 540, the display form of the index information and average moving velocity waveform described with reference to FIG. 5 is implemented.

According to the above description, an average moving velocity waveform is displayed in the area 530. However, this area may be configured not to display the average moving velocity waveform. In the example shown in FIG. 7, the area 540 displaying index information does not overlap another area. However, the area 540 may overlap the other area to such a degree that it does not interfere with image diagnosis by the operator.

Figure 10:
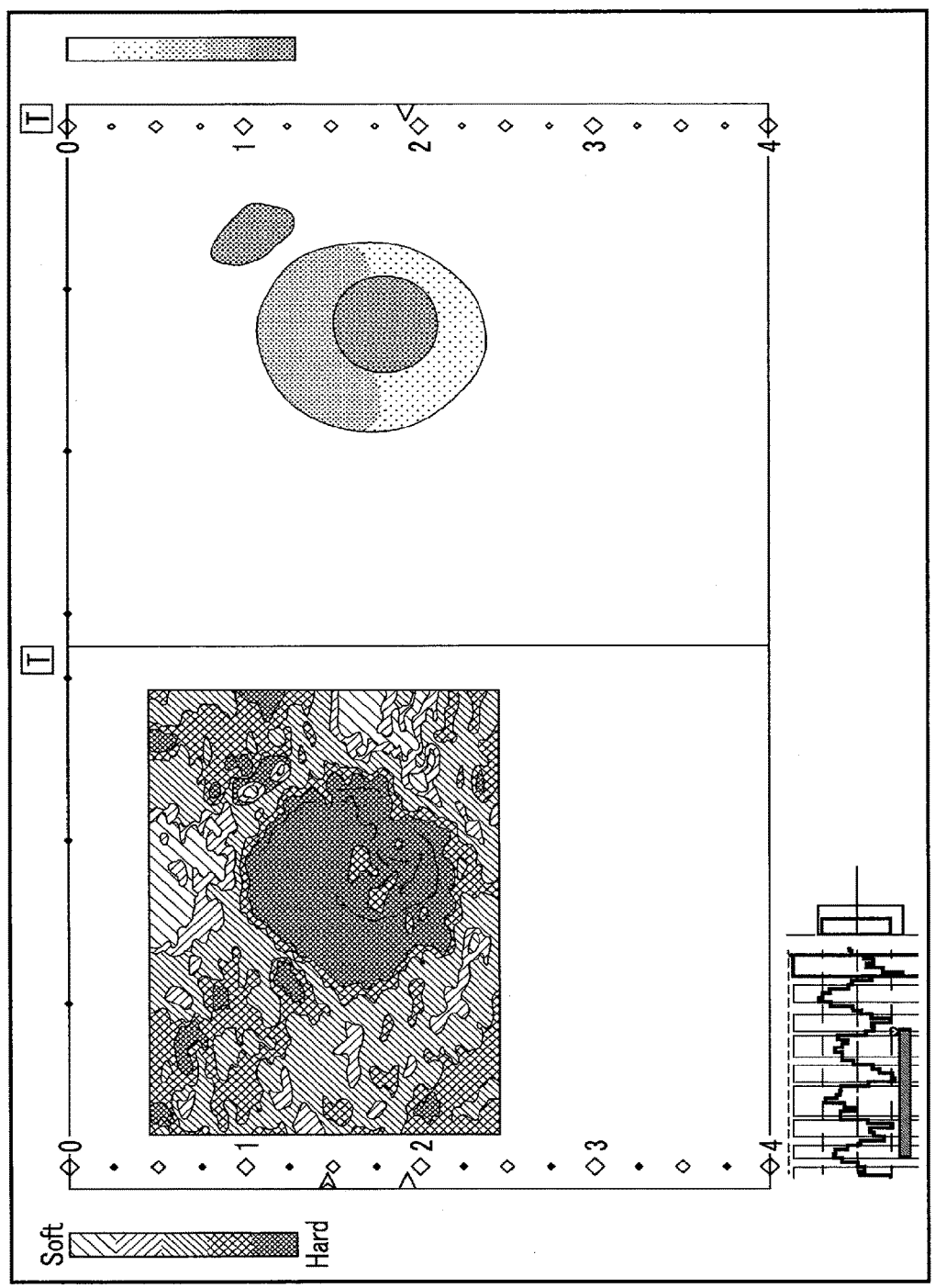
FIG. 10 is a view showing an example of a display form in the display area of a display according to the first embodiment.

FIG. 10 is a view showing an example of displaying a reference B-mode image, a strain image on which a B-mode image is superimposed, an average moving velocity waveform, and index information in the layout shown in FIG. 7. FIG. 11 is an enlarged view of the average moving velocity waveform and index information shown in FIG. 10. As shown in FIGS. 10 and 11, a dotted line indicating the maximum value of a velocity range and a dotted line indicating the average of velocity amplitude peaks as target information are superimposed and displayed on the average moving velocity waveform. In addition, index information (state information and target information) is displayed as, for example, a rectangle.

The length of an ordinate (first side) of a rectangle representing state information of index information indicates the average of velocity amplitude peaks (the average of the strengths (degrees) of pressurization/depressurization). The length of an abscissa (second side) of the rectangle representing the state information of the index information indicates the average cycle of compression/decompression (pressurization/depressurization) (average compression/decompression cycle). The length of an ordinate of a rectangle representing target information of the index information indicates the target average of velocity amplitude peaks (the target average of the strengths (degrees) of pressurization/depressurization). The length of an abscissa of the rectangle representing the state information of the index information indicates the target average cycle of compression/decompression (pressurization/depressurization) (target average compression/decompression cycle).

As described above, this embodiment is configured to transmit ultrasonic waves to an object via the ultrasonic probe 101 and receive reflected waves from the object as echo signals, thereby generating velocity distribution information concerning the object tissue for which compression (pressurization)/decompression (depressurization) has been performed by the operator using the ultrasonic probe 101 based on the echo signals. The embodiment is further configured to generate compression/decompression state information representing the strength (degree/magnitude) of compression/decompression by the operator and its cycle and compression/decompression target information representing the target strength and cycle of compression/decompression determined in advance based on the velocity distribution information and present the compression/decompression state information and the compression/decompression target information. This arrangement allows the operator to compress/decompress the object tissue while referring to the index information (compression/decompression state information and compression/decompression target information). This enables the operator to perform proper compression (pressurization)/decompression (depressurization). This enables the ultrasonic diagnostic apparatus 100 to obtain proper strain distribution information.

Note that this embodiment has exemplified the case in which the strength of compression/decompression by the operator and the target strength of compression/decompression are represented by the average moving velocity of the tissue. However, such a strength may be displayed by using the displacement, strain, strain ratio, or the like of the tissue which is calculated based on, for example, the above velocity distribution information.

In addition, in this embodiment, compression/decompression state information and compression/decompression target information have been described as graphic patterns which can be compared with each other with reference to FIG. 3. However, index information may be displayed in a different graphic pattern. The different graphic pattern includes, for example, an ellipse, triangle, rhombus, parallelogram, or a graphic pattern defined by a predetermined function (a Gaussian function or logistic function) whose shape is defined by two variables (the cycle of pressurization or depressurization and the degree of pressurization or depressurization). In addition, index information and target information may be output as audible sounds.

Figure 8:
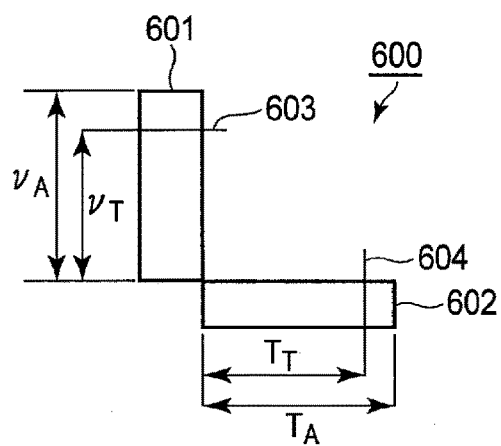
FIG. 8 is a view showing another example of the display form of index information displayed according to the first embodiment.

In this case, FIG. 8 is a view showing another example of the display form of index information displayed in graphics according to the first embodiment. In the example shown in FIG. 8, index information (a graphic pattern representing it) 600 is constituted by rectangular graphic patterns 601 and 602.

The graphic pattern 601 represents an average moving velocity $v_A$ of a tissue which corresponds to compression/decompression by the operator. The graphic pattern 602 represents a cycle $T_A$ of compression/decompression by the operator. The graphic patterns 601 and 602 are respectively provided with target lines 603 and 604. The target line 603 represents a target average moving velocity $v_T$ of the tissue which corresponds to compression/decompression. The target line 604 represents a target cycle $T_T$ of compression/decompression. The graphic patterns 601 and 602 are updated in accordance with the lapse of an ultrasonic diagnosis time like the graphic pattern 201 shown in FIG. 3 described above.

In the example shown in FIG. 8, unlike that shown in FIG. 3, when displaying the average moving velocity of a tissue which corresponds to compression/decompression by the operator and the target average moving velocity of the tissue, the average moving velocity (the degree of pressurization) at the time of compression is not differentiated from the average moving velocity (the degree of depressurization) at the time of decompression.

Even when index information is displayed in the form shown in FIG. 8, the operator can compare the average moving velocity of the tissue which corresponds to compression/decompression by the operator with the target average moving velocity of the tissue which corresponds to compression/decompression. In addition, the operator can perform ultrasonic diagnosis while comparing the cycle of compression/decompression by the operator with the target cycle of compression/decompression. This enables the ultrasonic diagnostic apparatus 100 to easily obtain proper strain distribution information.

In addition, this embodiment has exemplified the case in which index information is displayed (presented) by graphics. However, the index information may be displayed as numerical values. In this case, for example, the strength and cycle of compression/decompression by the operator and the target strength and cycle of compression/decompression are displayed as numerical values. In addition, the ultrasonic diagnostic apparatus 100 can also display index information both as graphics and numerical values. Furthermore, the ultrasonic diagnostic apparatus 100 can display index information in the form of a character string of one sentence. Moreover, the ultrasonic diagnostic apparatus 100 may output index information as audible sounds.

Second Embodiment

The second embodiment will be described next. Note that the arrangement of an ultrasonic diagnostic apparatus according to this embodiment is the same as that of the first embodiment described above, and hence will be described as needed with reference to FIG. 1. This embodiment will mainly describe differences from the first embodiment.

This embodiment differs from the first embodiment described above in that it presents whether the state (strength and cycle) of compression/decompression by the operator is proper.

In this embodiment, an index information generation unit 108 included in an ultrasonic diagnostic apparatus 100 compares generated compression/decompression state information with compression/decompression target information to determine whether the strength and cycle of compression/decompression by the operator, which are indicated by the compression/decompression state information, are proper.

More specifically, the index information generation unit 108 determines whether the strength of compression/decompression by the operation, which is indicated by the compression/decompression state information, falls within a predetermined range relative to the target strength of compression/decompression, which is indicated by the compression/decompression target information, i.e., the range from a lower limit $V_{TL}$ of the target strength to an upper limit $V_{TH}$ of the target strength.

Likewise, the index information generation unit 108 determines whether the cycle of compression/decompression by the operation, which is indicated by the compression/decompression state information, falls within a predetermined range relative to the target cycle of compression/decompression, which is indicated by the compression/decompression target information, i.e., the range from a lower limit $T_{TL}$ of the target cycle to an upper limit $T_{TH}$ of the target cycle.

The determination result obtained by the index information generation unit 108 described above is presented to the operator via a display controller 109 and a display 110.

The display form of a determination result (to be written as an index determination result hereinafter) obtained by the index information generation unit 108 will be described below. FIG. 9 shows an example of the layout of a display screen when displaying an index determination result according to this embodiment. As shown in FIG. 9, areas 710 to 740 are arranged on a display screen 700.

For example, a B-mode image is displayed in the area 710. A strain image is displayed in an area 711 provided in the area 710. That is, the strain image is displayed in the area 711 while being superimposed on the B-mode image.

In addition, an outer frame line 712 is displayed outside the area 711 in accordance with the above index determination result. More specifically, the outer frame line 712 is displayed outside the area 711 when the strength and cycle of compression/decompression by the operator are proper, i.e., when the strength of compression/decompression (e.g., the average moving velocity of the tissue) by the operator, which is indicated by compression/decompression state information, falls within a range determined in advance relative to the target strength of compression/decompression, which is indicated by compression/decompression target information (i.e., within the range from the lower limit of the target strength to the upper limit of the target strength), and the cycle of compression/decompression by the operator, which is indicated by the compression/decompression state information, falls within a range determined in advance relative to the target cycle of compression/decompression, which is indicated by the compression/decompression target information (i.e., within the range from the lower limit of the target cycle to the upper limit of the target cycle).

Note that the areas 720 to 740 are the same as the areas 520 to 540 described above with reference to FIG. 7, and hence a detailed description of them will be omitted.

As described above, this embodiment is configured to compare compression/decompression state information with compression/decompression target information to determine whether the strength and cycle of compression/decompression by the operator, which are indicated by the compression/decompression state information, are proper, and present the determination result (index determination result) to the operator. This allows the operator to easily recognize whether the state (operation) of compression/decompression by himself/herself is proper.

In addition, in this embodiment, as described with reference to FIG. 9, displaying an index determination result as the outer frame line 712 near the display area of a strain image (i.e., the area 711) enables the operator to confirm that the strength and cycle of compression/decompression by himself/herself are proper without averting his/her gaze from the strain image.

Note that this embodiment has exemplified the case in which the outer frame line 712 is displayed to present the operator information indicating that the strength and cycle of compression/decompression by the operator are proper, when the strength and cycle of compression/decompression by the operator fall within a predetermined range relative to a target strength and cycle. However, when one of the strength and cycle of compression/decompression by the operator is proper, the display form of the outer frame line 712 may be changed.

In addition, the outer frame line 712 may be displayed in different colors corresponding to the differences between the strength and cycle of compression/decompression by the operator and a target strength and cycle. In this case, a memory (not shown) stores a table (color map table) containing different colors corresponding to the degrees of differences (difference values) between the strength and cycle of compression/decompression by the operator and a target strength and cycle. This arrangement allows the operator to easily grasp the degrees of properness of the strength and cycle of compression/decompression by the operator.

Furthermore, referring to FIG. 9 described above, as in the first embodiment, the area 740 in which index information is displayed is arranged on the display screen 700. In this embodiment, however, since the operator can check whether the strength and cycle of compression/decompression by himself/herself are proper depending on whether the outer frame line 712 is displayed, the area 740 may be omitted.

In addition, this embodiment has exemplified the case in which an index determination result is displayed by the outer frame line 712. However, the index determination result may be displayed in another form. For example, the index determination result may be displayed as a character string. In addition, the index determination result may be output as audible sounds.

For example, the graphic patterns 601 and 602 described with reference to FIG. 8 may be arranged along the outer frame of the area 711, and the colors or the like of the graphic patterns 601 and 602 may be changed to present an index determination result (information indicating whether the strength and cycle of compression/decompression by the operator are proper) to the operator.

In addition, when displaying index information in the area 740 as in graphics or numerical values, the color or the like of the graphic pattern or numerical values may be changed to present the result to the operator.

According to the embodiments described above, it is possible to provide an ultrasonic diagnostic apparatus which enables the operator to properly perform compression/decompression.

In addition, each function according to the embodiments can be implemented by installing probe pressurization/depressurization information display programs for executing the corresponding processing in the computer of a workstation or the like and expanding them in the memory. In this case, the programs which can cause the computer to execute this method can be distributed by being stored in storage media such as magnetic disks (floppy disks, hard disks, and the like), optical disks (CD-ROMs, DVDs, and the like), and semiconductor memories. Note that the technical idea of this embodiment can be applied to MR elastography (to be referred to as MRE hereinafter). MRE is a technique of evaluating the hardness of a tissue in an object by MRI on a voxel basis.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasonic diagnostic apparatus, comprising:
an ultrasonic probe;
transmission/reception circuitry configured to transmit an ultrasonic wave to an object and receive a reflected wave from the object as an echo signal via the ultrasonic probe;
velocity distribution information generation circuitry configured to generate, based on the echo signal, velocity distribution information of a tissue in the object in accordance with an operation of pressurization or depressurization using the ultrasonic probe by an operator;
index information generation circuitry configured to generate state information representing a cycle of the pressurization or the depressurization of the operation and target information representing a target cycle of the pressurization or the depressurization of the operation, based on the velocity distribution information; and
a display configured to display the cycle in the form of a length of a second side in a predetermined graphic pattern representing the state information and the target information, the graphic pattern including a first side and the second side, display the state information and the target information as the graphic pattern, and display the graphic pattern upon changing the length of the second side of the graphic pattern in accordance with a change in the cycle of the pressurization or the depressurization in the state information.

2. The ultrasonic diagnostic apparatus of claim 1, wherein the index information generation circuitry is further configured to generate the state information, which further includes information indicating a degree of the pressurization or the depressurization of the operation, and generate the target information, which further includes information indicating a target degree that is a target value of the degree of the pressurization or the depressurization, and
the display displays the degree in the form of a length of the first side, displays the state information and the target information in the graphic pattern, and displays the graphic pattern upon changing the length of the first side of the graphic pattern in accordance with a change in the degree of the pressurization or the depressurization in the state information.

3. The ultrasonic diagnostic apparatus of claim 2, wherein the predetermined graphic pattern comprises a rectangle including the first side and the second side.

4. The ultrasonic diagnostic apparatus of claim 3, wherein the degree in the state information and the degree in the target information are determined from a displacement, a velocity, a strain, or a strain ratio of the tissue.

5. The ultrasonic diagnostic apparatus of claim 3, wherein the display displays the degree in the state information in the form of the length of the first side of the rectangle, and
displays the cycle in the state information in the form of the length of the second side of the rectangle, which is perpendicular to the first side.

6. The ultrasonic diagnostic apparatus of claim 3, wherein the display displays the rectangle upon changing unit length scales of two sides of the rectangle that are perpendicular to each other, in accordance with a type of the ultrasonic probe or a diagnosis target region in the object.

7. The ultrasonic diagnostic apparatus of claim 2, further comprising image generation circuitry configured to generate an image based on the echo signal,
wherein when a mode of displaying a plurality of images belonging to a predetermined period including a generation time point of the image is set, the index information generation circuitry is further configured to generate the state information based on the velocity distribution information in the predetermined period.

8. The ultrasonic diagnostic apparatus of claim 2, wherein the display displays the state information and the target information as the graphic pattern or as numerical values to be compared with each other.

9. The ultrasonic diagnostic apparatus of claim 2, further comprising waveform generation circuitry configured to generate a waveform representing a temporal change in the degree in the state information based on the velocity distribution information,
wherein the display further displays the waveform.

10. The ultrasonic diagnostic apparatus of claim 2, wherein the index information generation circuitry is further configured to determine whether the degree and the cycle in the state information are proper by comparing the state information with the target information, and
the display displays a determination result obtained by the index information generation circuitry.

11. The ultrasonic diagnostic apparatus of claim 2, wherein the index information generation circuitry is further configured to generate cycle instruction information for bringing the cycle in the state information close to the cycle in the target information, based on a difference value between the cycle in the state information and the cycle in the target information, and generate degree instruction information for bringing the degree in the state information close to the degree in the target information, based on a difference value between the degree in the state information and the degree in the target information, and
the display displays character strings concerning the cycle instruction information and the degree instruction information as one sentence in a display area different from the display areas of an image concerning the echo signal and the graphic pattern.

* * * * *